United States Patent [19]

Alaimo

[11] Patent Number: 4,540,693
[45] Date of Patent: Sep. 10, 1985

[54] THIOCYANATOQUINOXALINE COMPOUNDS WITH IMMUNOMODULATING ACTIVITY

[75] Inventor: Robert J. Alaimo, Norwich, N.Y.

[73] Assignee: Norwich Eaton Pharmaceuticals, Inc., New York, N.Y.

[21] Appl. No.: 531,320

[22] Filed: Sep. 12, 1983

[51] Int. Cl.³ ................ C07D 241/46; C07D 241/42; C07D 405/14; C07D 405/04
[52] U.S. Cl. .................... 514/249; 514/250; 514/885; 544/348; 544/353
[58] Field of Search ............... 544/353, 348; 424/250, 424/110

[56] References Cited

PUBLICATIONS

Singh, Chem. Abs., 93, 214633c (1980).

*Primary Examiner*—Mark L. Berch
*Attorney, Agent, or Firm*—Milton B. Graff, IV; Jack D. Schaeffer; Richard C. Witte

[57] ABSTRACT

New thiocyanatoquinoxaline compounds useful as immunomodulating agents which have the general formula:

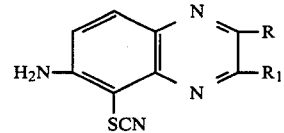

wherein R is hydrogen, methyl or 5-thiocyanato-2-furanyl; $R_1$ is hydrogen, methyl or 2-furanyl; or R and $R_1$ taken together completes a cyclohexyl ring.

11 Claims, No Drawings

THIOCYANATOQUINOXALINE COMPOUNDS WITH IMMUNOMODULATING ACTIVITY

BACKGROUND OF THE INVENTION

This invention is concerned with thiocyanatoquinoxaline derivatives that are useful as immunomodulating agents. More particularly this invention is concerned with compounds of the formula:

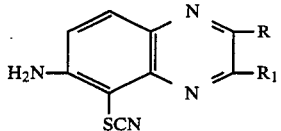

[Formula I]

wherein R is hydrogen, methyl, or 5-thiocyanato-2-furanyl; $R_1$ is hydrogen, methyl, or 2-furanyl; or R and $R_1$ taken together completes a cyclohexyl ring.

An immunomodulating agent is a substance which regulates or otherwise affects the immune response of a host. Compounds having such capability are useful as drugs for mitigating the immunological incompetence of a host body oftentimes encountered as an undesired side effect of cancer chemotherapy involving antineoplastic agents. Such depressed immune response lessens the protective function of the immune system permitting the invasion of pathogens such as viruses, bacteria and other parasites which otherwise could be resisted by the host.

Accordingly, there is a need to protect host that are being subjected to chemotherapy from the effects of having their immune system suppressed from such chemotherapy in order to avoid systemic infections which could be fatal.

It is an object of this invention to provide compounds which are useful as immunomodulating agents.

It is a further object of this invention to provide a method of alleviating the immunosuppressant activity of cancer chemotherapy.

SUMMARY OF THE INVENTION

The present invention is based on the discovery that compounds of Formula I exhibit immunomodulating activity in hosts that have been subjected to cancer chemotherapy.

These compounds can be formulated with a pharmaceutically acceptable carrier for systemic administration as described more fully hereinafter.

DETAILED DISCUSSION

The compounds of Formula I exhibit salutary effect upon the immune system of an animal with respect to resistance to bacterial infection when such system has been depressed by administration of an antineoplastic agent that is used in cancer chemotherapy. Thus, 80% or more of mice administered intraperitoneally 100 mg/kg of cyclophosphamide 4 days before being inoculated intravenously with $1 \times 10^5$ cells of *Pseudomonas aeruginosa* died. In mice not receiving cyclophosphamide, the mortality was less than 10%. When the compounds of this invention were administered at a level of 80 mg/kg subcutaneously to cyclophosphamide (100 mg/kg) treated mice 4 and 2 days before inoculation with *Pseudomonas aeruginosa*, the mortality was 0% to about 15%.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixers. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a long period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyoxyethylene sorbitan monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents may also be present.

The preferred thiocyanatoquinoxaline derivatives are: 6-Amino-2,3-dimethyl-5-thiocyanatoquinoxaline; 6,7,8,9-tetrahydro-1-thiocyanato-2-phenazinamine; 3-(2-furanyl)-5-thiocyanato-2-(5-thiocyanato-2-furanyl)-6-quinoxalinamine.

In order that this invention may be readily available to those skilled in the art these illustrative examples are appended.

EXAMPLE I

6-Amino-2,3-dimethyl-5-thiocyanotoquinoxaline

A. 2,3-Dimethyl-6-nitroquinoxaline

A stirred mixture of 4-nitro-o-phenylenediamine (Fairmont) (105 g, 0.69 mole) and 2,3-butanedione (Aldrich) (59 g, 0.69 mole) in 1.5 L of SDA-32 was heated at reflux for 4 hours. The reaction mixture was let stand at room temperature overnight. The crystallized intermediate was chilled and collected to give after ether wash 62.9 g (44.9%) of known solid. The intermediate was used without further purification in step B.

B. 6-Amino-2,3-dimethylquinoxaline

A near solution of 2,3-dimethyl-6-nitroquinoxaline (62.9 g, 0.31 mole) in 1 L of absolute alcohol (Mallinkrodt) was hydrogenated in Parr apparatus using 5% Palladium on carbon 50% wet catalyst (Englehard). Hydrogen uptake (100% of theory) in 2 hours was noted. After the reduction stopped the catalyst was removed by filtration and the filtrate remaining concentrated to dryness in vacuo. The residue remaining was used without further purification as an intermediate in part C. Yield 52 g (96%).

C. 6-Amino-2,3-dimethyl-5-thiocyanatoquinoxaline

To a stirred mixture of sodium thiocyanate (Mallinkrodt) 122 g, 1.5 mole) in 500 ml of anhydrous methanol (Mallinkrodt) maintained at $-10°$ was added dropwise a chilled mixture of bromine (Fisher) (40 ml, 0.75 mole) in a methanol/sodium bromide (Mallinkrodt) saturated solution (100 ml). After the addition was complete 6-amino-2,3-dimethylquinoxaline (52 g, 0.3 mole) was added to the $-10°$ reaction solution. During the additions and for 4 hours after the reaction temperature was maintained at $-10°$ by means of a dry ice/acetone bath. The reaction mixture was allowed to warm to room temperature and filtered. The solid was treated with 1 L of water followed by the addition of concentrated NH4OH to a pH of 8. The basic mixture was filtered to give 25 g (36%) of product.

An analytical sample was prepared by two recrystallizations from $CH_3NO_2$ (DARCO) m.p. 207–209 corr.

Anal. Calcd. for $C_{11}H_{10}N_4S$: C, 57.37; H, 4.38; N, 24.33. Found: C, 57.32; H, 4.39; N, 24.31.

EXAMPLE II 6,7,8,9-Tetrahydro-1-thiocyanato-2-phenazinamine

A. 6,7,8,9-Tetrahydro-2-nitrophenazine

A mixture of 4-nitro-o-phenylenediamine (33.7 g, 0.22 mole) and 25.0 g (0.22 mole) of 1,2-cyclohexanedione in 500 ml of SDA#32 was heated at reflux for 24 hours. The reaction mixture was then stored overnight at room temperature and then filtered. The brown crystalline solid was then washed with ether, air dried, and dried to a consistent weight at 60°, m.p. 175°–178°. Yield: 22 g (96%).

B. 6,7,8,9-Tetrahydro-2-phenazinamine

A 18.0 g (0.078 mole) portion of 6,7,8,9-tetrahydro-2-nitrophenazine and 5 g of 5% Pd/C (50% H2O) were placed in a 1.7 liter stainless steel pressure bottle and subjected to hydrogenation at 40 psig. The hydrogen uptake was 18 lb (theory 17 lb). The reaction mixture was then filtered and concentrated. The filtrate was then concentrated to ⅓ volume, refrigerated, filtered, air dried, and dried to a constant weight at 60° to give 15 g (94%) of a yellow solid, m.p. 150°–152°.

C. 6,7,8,9-Tetrahydro-1-thiocyanato-2-phenazinamine

To a stirred mixture of sodium thiocyanate (26.5 g, 0.33 mole) in 150 ml of anhydrous methanol maintained at $-10°$ was added dropwise a chilled mixture of bromine (8.7 ml, 0.30 mole) in 21 ml of methanol/saturated sodium bromide solution. To this mixture was added immediately at $-10°$ a 13 g (0.065 mole) portion of 6,7,8,9-tetrahydro-2-phenazinamine. The reaction was maintained at $-10°$ (via a dry ice/acetone bath) for 4 hours, warmed to room temperature, diluted with 250 ml of distilled H2O, basified with NH4OH to a pH of 8 and filtered. The yellow-brown solid was air dried and dried to a constant weight at 60°, m.p. 266°–270° dec. Yield: 8.0 g (48%).

An analytical sample was prepared by recrystallization from acetonitrile at 3 ml/g, m.p. 272°–274° dec.

Anal. Calcd. for $C_{13}H_{12}N_4S$: C, 60.92; H, 4.72; N, 21.86. Found: C, 60.54; H, 4.58; N, 21.94.

EXAMPLE III 3-(2-Furanyl)-5-thiocyanato-2-(5-thiocyanato-2-furanyl)-6-quinoxalinamine A. 2,3-di(1-furanyl)-6-nitroquinoxaline 46 g (0.3 mole) 4-nitro-o-phenylenediamine was mixed with 56 g (0.3 mole) furil in 1200 ml ethanol and refluxed for 20 hours. The mixture was then cooled in ice; the product filtered, washed with ethanol and air dried; 87 g (95%) brown crystals were obtained.

The crude product was recrystallized from about 900 ml nitromethane with charcoal (Darco); 74 g (81%) golden yellow needles were obtained.

B. 6-(amino-2,3-di(1-furanyl)quinoxaline 16 g of the product from part A was reduced in 200 ml of ethanol over 0.5 g 5% Pd/C containing 50% water; a 12 PSI pressure drop in about 3 hours was noted (calculated=13). The catalyst and product were filtered. The product dissolved in warm dimethyl formamide, and catalyst filtered. The combined filtrates were concentrated under vacuum to about ½ original volume and water was added to precipitate the product. The product (B) was filtered, washed with ethanol and air dried to give 11 g of yellow crystalline solid.

C. 3-(2-Furanyl)-5-thiocyanato-2-(5-thiocyanato-2-furanyl)-6-quinoxalinamine

A mixture of sodium thiocyanate (15 g, 0.19 mole) was dissolved in anhydrous methanol (75 ml). The solution was chilled to $-10°$ and a chilled mixture of bromine (6 ml) in sodium bromide saturated methanol (25 ml) was added dropwise over a 10-minute period. Following the addition, a single portion of 6-amino-2,3-di-2-furylquinoxaline (5798-9A) (9.4 g, 0.034 mole) was added and the mixture stirred below −10° for several hours. The reaction mixture was allowed to warm to room temperature. Following filtration, the solid was suspended in ice water (500 ml) and made basic with ammonium hydroxide. Following filtration, the solid was recrystallized from nitromethane to give 11 g (78%) of product which melted at 185°–187°.

Anal. Calc'd. for $C_{18}H_9N_5O_2S_2$: C, 55.23; H, 2.32; N, 17.89. Found: C, 55.25; H, 2.25; N, 17.84.

EXAMPLE IV

In this Example the effects of the compounds of this invention on the immunoresponse system of mice is demonstrated according to a known procedure using mice in which their immunity to bacterial infection was suppressed by a cytotoxic agent.

Thus mice were dosed with the compounds of this invention 4 days and again 2 days (subcutaneously) before intravenous infection with $10^6$ *Pseudomonas aeruginosa*. Cyclophosphamide, a cytotoxic agent, was given to experimental and control groups of mice by the intraperitoneal route at a dose of 150 mg/kg 4 days before the infection. The pharmaceutical formulation was made pursuant to Example V.

The test results obtained are set out in Table I below. In the Table the results are expressed in terms of percent protection calculated by the equation:

$$\% \text{ protection} = \frac{(\% \text{ dead in control group}) - (\% \text{ dead in experimental group})}{\% \text{ dead in control group}} \times 100$$

TABLE I

| Example Compound | Mg/Kg Dose | ACTIVITY Experimental Dead/Total | Control Dead/Total | % Protection |
|---|---|---|---|---|
| I | 40 | 2/19 | 13/20 | 83 |
|  | 20 | 9/65 | 33/64 | 73 |
|  | 10 | 14/38 | 25/36 | 46 |
|  | 5 | 17/40 | 25/36 | 38 |
|  | 1 | 32/37 | 25/36 | 0 |
| II | 20 | 1/10 | 9/10 | 89 |
|  | 5 | 8/10 | 10/10 | 20 |
|  | 1 | 10/10 | 10/10 | 0 |
|  | .5 | 9/10 | 10/10 | 10 |
| III | 20 | 1/10 | 9/10 | 89 |
|  | 5 | 12/20 | 19/20 | 37 |
|  | 1 | 17/20 | 19/20 | 11 |
|  | .5 | 10/10 | 10/10 | 0 |

EXAMPLE V

Parental Formulation 0.8 mg of a compound of Formula I was suspended in pyrogen free distilled water to give 0.5 ml suspension, which was then subjected to sonification.

What is claimed is:

1. A compound of the formula:

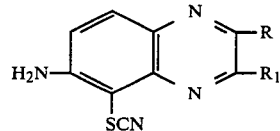

wherein R is hydrogen, methyl or 5-thiocyanato-2-furanyl; $R_1$ is hydrogen, methyl or 2-furanyl; or R and $R_1$ taken together with the atoms to which they are attached form a cyclohexyl ring.

2. A compound according to claim 1 wherein R and $R_1$ are methyl.

3. A compound according to claim 1 wherein R is 5-thiocyanato-2-furanyl and $R_1$ is 2-furanyl.

4. A compound according to claim 1 wherein R and $R_1$ taken together with the atoms to which they are attached form a cyclohexyl ring.

5. A method for mitigating the immunological incompetence of a host which comprises administering to a host in need of such treatment an effective amount of a pharmaceutical composition comprising a compound of the formula:

wherein R is hydrogen, methyl, or 5-thiocyanato-2-furanyl; $R_1$ is hydrogen, methyl or 2-furanyl; or R and $R_1$ taken together with the atoms to which they are attached form a cyclohexyl ring.

6. A method according to claim 5 in which the compound is the compound of Formula I wherein R and $R_1$ both represent methyl.

7. A method according to claim 5 in which the compound is the compound of Formula I wherein R is 5-thiocyanato-2-furanyl and $R_1$ is 2-furanyl.

8. A method according to claim 5 in which the compound is the compound of Formula I wherein R and $R_1$ taken together with the atoms to which they are attached form a cyclohexyl ring.

9. A method according to claim 5 in which the effective amount is 20–40 mg/kg weight of the host.

10. A method according to claim 5 wherein the immunological incompetence of the host is caused by cancer chemotherapy.

11. A pharmaceutical composition useful as an immunomodulating agent, comprising as active ingredient an effective amount of a compound of the formula:

wherein R is hydrogen, methyl or 5-thiocyanato-2-furanyl; $R_1$ is hydrogen, methyl or 2-furanyl; or R and $R_1$ taken together with the atoms to which they are attached form a cyclohexyl ring; with a pharmaceutically acceptable carrier or adjuvant.

* * * * *